United States Patent [19]

Krishnamurthy

[11] Patent Number: 4,827,019

[45] Date of Patent: May 2, 1989

[54] STERICALLY HINDERED AROMATIC CARBOXYLIC ESTERS

[75] Inventor: Sundaram Krishnamurthy, Penfield, N.Y.

[73] Assignee: Eastman Kodak Company, Rochester, N.Y.

[21] Appl. No.: 2,356

[22] Filed: Jan. 12, 1987

Related U.S. Application Data

[62] Division of Ser. No. 813,307, Dec. 24, 1985, Pat. No. 4,684,606.

[51] Int. Cl.[4] .................... C07C 69/80; C07D 213/78; C07D 209/04; C07D 307/02

[52] U.S. Cl. .................................... 560/84; 430/546; 546/301; 548/491; 548/556; 549/79; 549/491; 560/76; 560/83; 560/85; 560/86

[58] Field of Search ..................... 560/76, 83, 84, 85, 560/86, 103, 106, 107, 109; 546/301; 548/491, 556; 549/79, 499

[56] References Cited

U.S. PATENT DOCUMENTS

| | | | |
|---|---|---|---|
| 1,415,340 | 5/1922 | Haller | 560/84 X |
| 1,702,188 | 2/1929 | Young | 560/76 |
| 2,015,077 | 9/1935 | Lawson | 560/76 |
| 2,047,664 | 7/1936 | Barrett et al. | 560/84 |
| 2,322,027 | 6/1943 | Jelley et al. | 430/546 |
| 2,425,173 | 8/1947 | Bruson | 560/84 X |
| 2,535,643 | 12/1950 | Mack | 560/84 X |
| 2,692,277 | 10/1954 | Nelson | 560/84 |
| 3,021,357 | 2/1962 | Swakon | 560/76 |
| 3,076,837 | 2/1963 | Mills | 560/86 |
| 3,475,172 | 10/1969 | Bright et al. | 430/546 X |
| 3,779,765 | 12/1973 | McCrossen et al. | 430/546 X |
| 4,193,802 | 3/1980 | Mukunoki et al. | 430/139 |
| 4,308,328 | 12/1981 | Salyer et al. | 430/17 |
| 4,327,175 | 4/1982 | Toda et al. | 430/546 |
| 4,407,940 | 10/1983 | Nakamura et al. | 430/546 |
| 4,451,558 | 5/1984 | Sugita et al. | 430/546 |
| 4,543,420 | 9/1985 | Godwin et al. | 560/76 |

FOREIGN PATENT DOCUMENTS

| | | |
|---|---|---|
| 149348 | 6/1968 | Japan . |
| 1274523 | 8/1969 | United Kingdom . |

OTHER PUBLICATIONS

Chemical Abstracts, vol. 59, 7910b, Sep. 1963.

Chemical Abstracts, vol. 62, 8917f, Sep. 1965.

*Primary Examiner*—Werren B. Lone

*Assistant Examiner*—Vera C. Clarke

*Attorney, Agent, or Firm*—Harold E. Cole

[57] ABSTRACT

Photographic coupler solvents comprising aromatic carboxylic esters such as phthalates and isophthalates having bulky or branched ester substituents are described for incorporation in photographic emulsions and elements. The solvents are preferably employed in the cyan layer to protect the cyan dye against ferrous ion reduction. The solvents also provide improvements in yellow dye stability to light, cyan dye stability in the dark and magenta dye stability to heat and light.

12 Claims, No Drawings

STERICALLY HINDERED AROMATIC CARBOXYLIC ESTERS

This is a division of application Ser. No. 813,307, filed Dec. 24, 1985, now U.S. Pat. No. 4,684,606.

This invention relates to photographic coupler solvents and to silver halide photographic elements employing such coupler solvents. In a particular aspect, it relates to coupler solvents comprising aromatic carboxylic esters, and particularly phthalates and isophthalates, having bulky or branched ester substituents.

Images are commonly obtained in the photographic art by a coupling reaction between the development product of a silver halide color developing agent (i.e., oxidized aromatic primary amino developing agent) and a color forming compound commonly referred to as a coupler. The dyes produced by coupling are indoaniline, azomethine, indamine or indophenol dyes, depending upon the chemical composition of the coupler and the developing agent. The subtractive process of color formation is ordinarily employed in multicolor photographic elements and the resulting image dyes are usually cyan, magenta and yellow dyes which are formed in or adjacent to silver halide layers sensitive to radiation complementary to the radiation absorbed by the image dye; i.e. silver halide emulsions sensitive to red, green and blue radiation.

The patent and technical literature is replete with references to compounds which can be used as couplers for the formation of photographic images. Preferred couplers which form cyan dyes upon reaction with oxidized color developing agents are phenols and naphthols. Representative couplers are described in the following patents and publications: U.S. Pat. Nos. 2,772,162, 2,895,826, 3,002,836, 3,034,892, 2,474,293, 2,423,730, 2,367,531, 3,041,236, 4,333,999 and "Farbkuppler-eine Literaturubersicht," published in Agfa Mitteilungen, Band II, pp. 156–175 (1961).

Preferred couplers which form magenta dyes upon reaction with oxidized color developing agent are pyrazolones, pyrazolotriazoles, pyrazolobenzimidazoles and indazolones. Representative couplers are described in such patents and publications as U.S. Pat. Nos. 2,600,788, 2,369,489, 2,343,703, 2,311,082, 2,673,801, 3,152,896, 3,519,429, 3,061,432, 3,062,653, 3,725,067, 2,908,573 and "Farbkuppler-eine Literaturubersicht," published in Agfa Mitteilungen, Band II, pp. 126–156 (1961).

Couplers which form yellow dyes upon reaction with oxidized color developing agent are acylacetanilides such as benzoylacetanilides and pivalylacetanilides. Representative couplers are described in the following patents and publications: U.S. Pat. Nos. 2,875,057, 2,407,210, 3,265,506, 2,298,443, 3,048,194, 3,447,928 and "Farbkuppler-eine Literaturubersicht," published in Agfa Mitteilungen, Band II, pp. 112–126 (1961).

When intended for incorporation in photographic elements, couplers are commonly dispersed therein with the aid of a high boiling organic solvent, referred to as a coupler solvent. Couplers are rendered nondiffusible in photographic elements, and compatible with coupler solvents, by including in the coupler molecule a group referred to as a ballast group. This group normally is located on the coupler in a position other than the coupling position and imparts to the coupler sufficient bulk to render the coupler nondiffusible in the element as coated and during processing. It will be appreciated that the size and nature of the ballast group will depend upon the bulk of the unballasted coupler and the presence of other substituents on the coupler.

During photofinishing, developing agent sometimes gets carried over and mixed into the bleach solution which results in reduction of ferric ion complexes in the bleach solution to ferrous ion complexes. These ferrous ions then have a tendency to reduce the cyan dye and convert it to a leuco form, causing a loss in dye density. Any alleviation of this problem would be most desirable.

The high boiling solvents of phthalic ester compounds, e.g. dibutyl phthalate, and phosphoric ester compounds, e.g., tricresyl phosphate, have often been used as coupler solvents because of their coupler-dispersing ability, inexpensiveness and availability. Such compounds are described in Jelley et al, U.S. Pat. No. 2,322,027. However, these conventional coupler solvents do not solve the ferrous ion reduction of cyan dye problem, as will be shown by comparative tests hereinafter.

There are other prior art references which also disclose closely related compounds to those of the invention. *Research Disclosure,* 16744, March 1978, page 13, discloses di-t-butyl phthalate and di-isopropyl phthalate. U.S. Pat. No. 4,407,940 discloses di-t-octyl phthalate. British Pat. No. 1,274,523 and U.S. Pat. No. 3,779,765 disclose di(2-ethylhexyl)phthalate. U.S. Pat. No. 3,475,172 describes high-boiling solvent esters derived from phthalic, isophthalic or terephthalic acids and alkyl-substituted cyclohexanols, while those shown in U.S. Pat. No. 3,779,765 are derived from benzenetricarboxylic acids and certain branched-alkyl alcohols. Japanese patent application No. 59/149348 cites a number of branched and straight-chain alkyl phthalate esters said to be useful for dispersing certain hydroquinone derivatives. U.S. Pat. Nos. 4,193,802 and 4,327,175 disclose high-boiling solvents in which an aromatic ring is substituted by up to six ester groups comprising cyclic saturated hydrocarbon residues. However, as before, these compounds are not as effective as Applicant's compounds in lessening the ferrous ion reduction of cyan dye problem, as will be shown by comparative tests hereinafter.

It would be desirable to provide a new class of coupler solvents useful in color photographic materials, particularly those having cyan couplers. It would also be desirable to provide such solvents which markedly reduce the tendency of ferrous ions to reduce cyan dye. Further, it would be desirable to provide such coupler solvents which would provide improvement in yellow dye stability to light, cyan dye stability in the dark and magenta dye stability to heat and light.

These and other objects are achieved in accordance with the invention which comprises a photographic element comprising a support having thereon at least one silver halide emulsion layer having associated therewith a dye-forming coupler and a coupler solvent therefor having the formula:

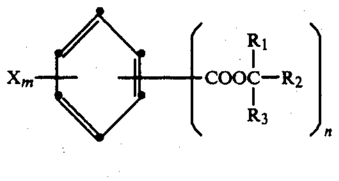

wherein each X may independently represent a halogen atom, an alkyl group of from 1 to about 20 carbon atoms, an alkoxy group of from 1 to about 20 carbon atoms, or a carboxylic ester;

m represents an integer of 0 to 5;

n represents an integer of 1 to 4; and $R_1$, $R_2$, and $R_3$ each independently represents a substituted or unsubstituted alkyl group having from 1 to about 10 carbon atoms such as methyl, trifluoromethyl, ethyl, isopropyl, isohexyl, sec-butyl, sec-heptyl or dodecyl; a substituted or unsubstituted alicyclic group, saturated or partially saturated, having from 3 to about 12 carbon atoms such as cyclopropyl, cyclobutyl, cyclohexyl, 4-methylcyclohexylene, 4-methyl-cyclohexyl, cycloheptyl or decahydro-2-naphthyl; a substituted or unsubstituted aralkyl group having from about 7 to about 20 carbon atoms such as benzyl, 4-methoxybenzyl or 1-naphthylmethyl; a substituted or unsubstituted aryl group having from about 6 to about 20 carbon atoms such as phenyl, 4-methoxyphenyl, 2,4-dichlorophenyl or naphthyl; a substituted or unsubstituted heterocyclyl group having from 3 to about 10 carbon atoms such as furyl, thienyl, pyridyl, N-methylpyrrolyl, tetrahydrofurfuryl or N-ethyl indolyl; or may be combined together to form one or more rings having from 4 to about 10 non-metallic ring atoms such as 3-acetoxy-2,2,4,4-cyclobutyl, 1-methylcyclopentyl, 1-butylcyclohexyl, 1-ethyltetralyl, 2-pinanyl, fenchyl or 3-methyl menthyl;

with the proviso that the alpha hydrogens of $R_1$, $R_2$ and $R_3$ total no more than seven; and with the further proviso that $R_1$ can additionally be hydrogen when (a) $R_2$ and $R_3$ join together to form a ring substituted by no more than one alpha hydrogen or (b) when $R_2$ and $R_3$ do not join to form a ring and if at least one of $R_2$ or $R_3$ contains an alpha carbon having two different non-hydrogen substituents.

In a preferred embodiment of the invention, m in the above formula is O, n is 2 and the ester groups are located ortho or meta to each other as follows:

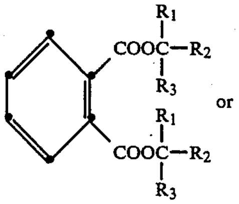
or
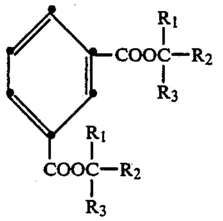

wherein $R_1$, $R_2$ and $R_3$ are defined as above.

In another preferred embodiment of the invention, the dye-forming coupler forms a cyan dye upon reaction with oxidized color developing agent, the coupler being a phenol or a naphthol, and the coupler and coupler solvent are located in the silver halide emulsion layer.

In still another preferred embodiment of the invention, $R_1$ is hydrogen or an alkyl group of from 1 to about 10 carbon atoms, $R_2$ is an alkyl group of from 1 to about 10 carbon atoms, $R_3$ is an alkyl or substituted alkyl group of from 2 to about 12 carbon atoms, an alicyclic group of from 3 to about 12 carbon atoms, a heterocyclyl group of 3 to about 10 carbon atoms or an aryl or substituted aryl group of 6 to about 20 carbon atoms, or $R_2$ and $R_3$ are combined together to form a ring of about 4 to about 10 atoms.

In yet another preferred embodiment of the invention, $R_1$ and $R_2$ are the same or different alkyl or substituted alkyl groups containing from 1 to about 10 carbon atoms and $R_3$ is an alkyl group containing from 2 to about 12 carbon atoms.

In still yet another preferred embodiment of the invention, $R_1$ is an alkyl group of from 1 to about 10 carbon atoms and $R_2$ and $R_3$ are combined together to form a ring of 6 carbon atoms.

In another preferred embodiment of the invention, $R_1$, $R_2$ and $R_3$ are each ethyl.

In another preferred embodiment of the invention, $R_1$ is hydrogen or methyl, $R_2$ is methyl, and $R_3$ is

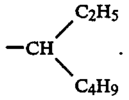

In another preferred embodiment of the invention, $R_1$ and $R_2$ are each methyl and $R_3$ is

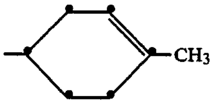
or
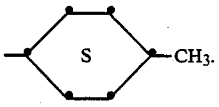

In another preferred embodiment of the invention, $R_1$ is ethyl, $R_2$ is methyl and $R_3$ is $$-CH_2CH_2CH_2\underset{CH_3}{\underset{|}{CH}}-CH_3.$$

In another preferred embodiment of the invention, $R_1$ is hydrogen or butyl and $R_2$—C—$R_3$ forms the fenchyl group

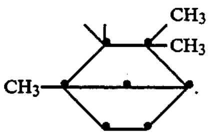

In another preferred embodiment of the invention, $R_1$ is methyl and $R_2$ and $R_3$ form a cyclohexyl ring.

In another preferred embodiment of the invention $R_1$ is methyl and $R_2$—C—$R_3$ forms the menthyl group

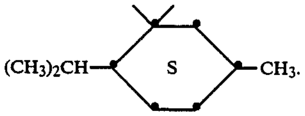

In another preferred embodiment of the invention, $R_1$ is hydrogen, $R_2$ is methyl and $R_3$ is phenyl.

Preferred compounds included within the scope of the invention include the following

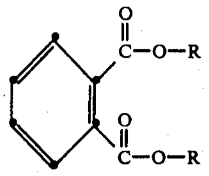
R
1. 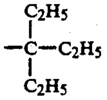
2. 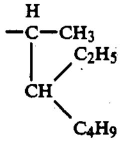
3. 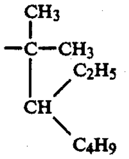
4. 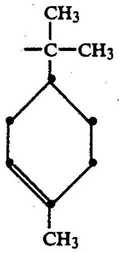
5. 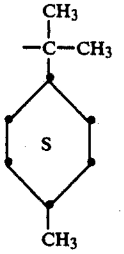
6. 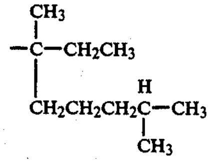
7. 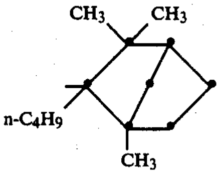
8. 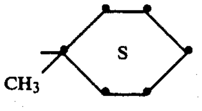
-continued
9. 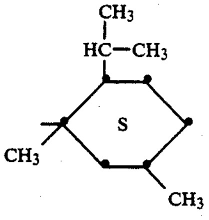
10. 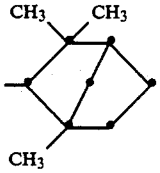
11. 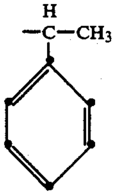
12. 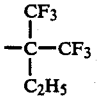
13. 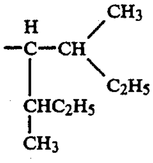
14. 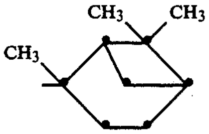
15. 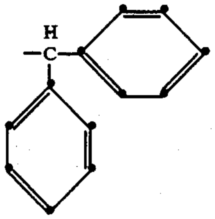
16. 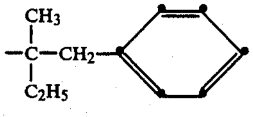
17. 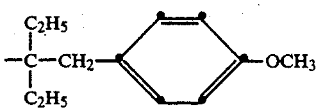
18. 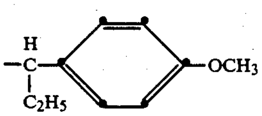

-continued
19.
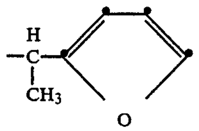
20.
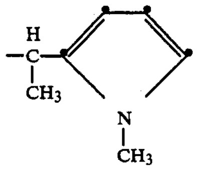
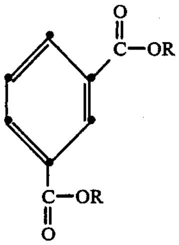
R
21.
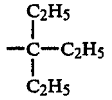
22.
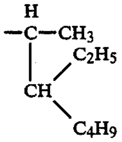
23.
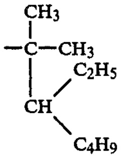
24.
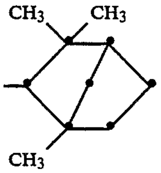
25.
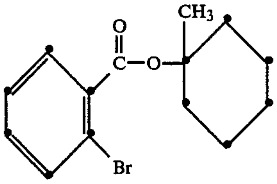
26.
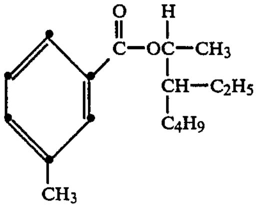
-continued
27.
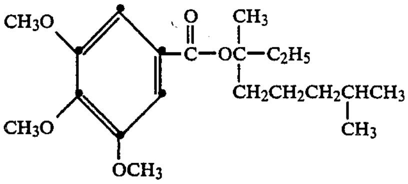
28.
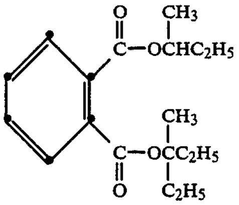
29.
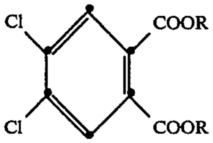
wherein R is 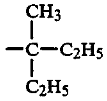
30.
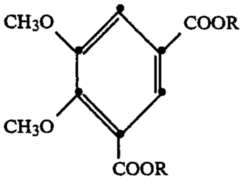
wherein R is 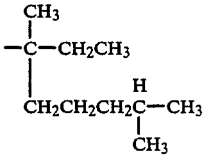
31.
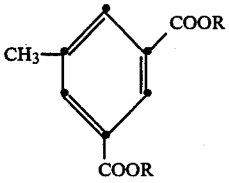
wherein R is 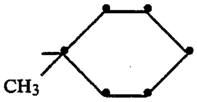
32.
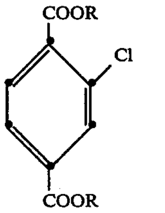

-continued wherein R is 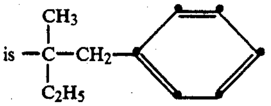

33.

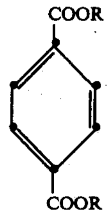

wherein R is 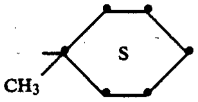

34.

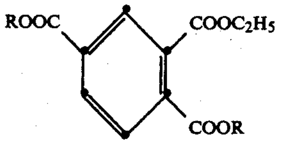

wherein R is 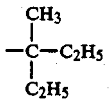

35.

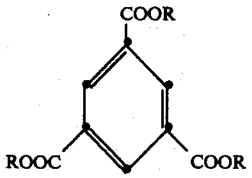

wherein R is 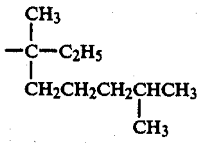

36.

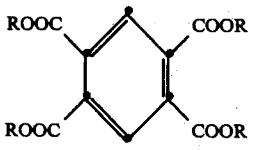

wherein R is 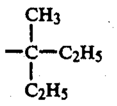

As previously noted in the proviso following the general structural formula for compounds of the invention, the alpha hydrogens of $R_1$, $R_2$ and $R_3$ must total no more than seven. In the following structures representing the alkyl portion of phthalate ester examples, each alpha carbon is designated with an arrow. It can be seen that the hydrogen substituents on these carbons total six and seven, respectively, for Compounds 1 and 3 of this invention but more than seven for comparison solvent CS-5, employed in the examples hereinafter.

| Compound 1 (6H) | Compound 3 (7H) | CS-5 (9H) |
|---|---|---|
| 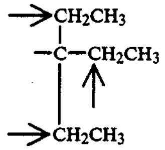 | 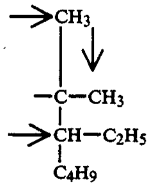 | 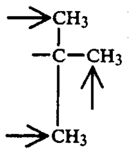 |

A similar illustration can be made for the other proviso following the general formula that $R_1$ can additionally be hydrogen when:

(a) $R_2$ and $R_3$ join together to form a ring substituted by no more than one alpha hydrogen or (b) $R_2$ and $R_3$ do not join to form a ring and if at least one of $R_2$ or $R_3$ contains an alpha carbon having two different non-hydrogen substituents.

In the following structures, $R_1$ is hydrogen (designated *H) and the alpha carbons are marked with arrows.

It can be seen for ring compounds that Compound 10 of the invention contains no alpha hydrogen substituents, while each of two prior art solvents (designated as Compounds 8 and 9, respectively, in U.S. Pat. No. 4,193,802), contains more than one alpha hydrogen.

Compound 10 (no H)

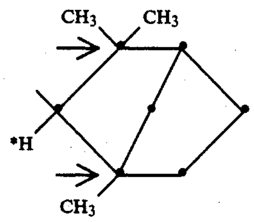

Prior Art Compound (2H)

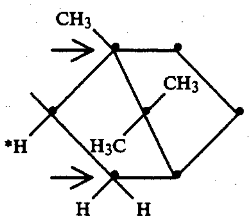

Prior Art Compound CS-15 (3H)

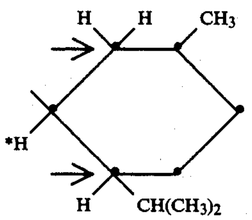

For branched chain structures of Compounds 2 and 13 of the invention, the alpha carbon of $R_3$, marked by the horizontal arrow, has two different alkyl substituents while a prior art compound (designated HBS-5 in Japanese patent application No. 59/149,348) is outside the invention because the two non-hydrogen alpha substituents in $R_3$ are identical.

| Compound 2 | Compound 13 | Prior Art Cmpd. |
|---|---|---|
| 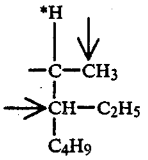 | 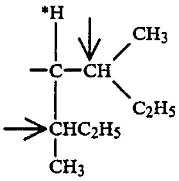 | 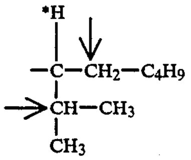 |

The above compounds may be synthesized by combining bulky and branched alkanols or cycloalkanols with the appropriate aromatic carboxylic acid derivatives, such as derivatives of benzoic, phthalic, isophthalic, terephthalic, benzenetricarboxylic, or benzenetetracarboxylic acids.

The coupler solvents of this invention can be used in the ways and for the purposes that coupler solvents are used in the photographic art. They may be used in any concentration which is effective for the intended purpose. Generally, good results can be obtained using concentrations ranging from 0.1 to 1.0 g/$m^2$, preferably from 0.2 to 0.4 g/$m^2$.

Typically, the coupler solvent and coupler are incorporated in a silver halide emulsion and the emulsion coated on a support to form a photographic element. Alternatively, the coupler solvent and coupler can be incorporated in photographic elements adjacent to the silver halide emulsion where, during development, the coupler will be in reactive association with development products such as oxidized color developing agent. Thus, as used herein, the term "associated therewith" signifies that the coupler solvent and coupler are in the silver halide emulsion layer or in an adjacent location where, during processing, they will come into reactive association with silver halide development products.

Photographic elements of the invention can be single color elements or multicolor elements. Multi-color elements contain dye image-forming units sensitive to each of the three primary regions of the visible spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer, e.g., as by the use of microvessels as described in Whitmore U.S. Pat. No. 4,362,806 issued Dec. 7, 1982.

A typical multicolor photographic element of the invention comprises a support having thereon a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler, at least one of the couplers in the element being dissolved in a coupler solvent of this invention. The element can contain additional layers, such as filter layers, interlayers, overcoat layers, subbing layers, and the like.

In the following discussion of suitable materials for use in the emulsions and elements of this invention, reference will be made to *Research Disclosure,* December 1978, Item 17643, published by Industrial Opportunities Ltd., Homewell Havant, Hampshire, PO9 1EF, U.K., the disclosures of which are incorporated herein by reference. This publication will be identified hereafter by the term "Research Disclosure".

The silver halide emulsions employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers generally described above, the elements of the invention can include additional couplers as described in Research Disclosure Section VII, paragraphs D, E, F and G and the publications cited therein. These couplers can be incorporated in the elements and emulsions as described in Research Disclosure Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizers (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p-phenylene diamines. Especially preferred are 4-amino-N,N-diethyl-aniline hydrochloride, 4-amino-3-methyl-N,N-diethylaniline hydrochloride, 4-amino-3-methyl-N-ethyl-N-$\beta$-(methanesulfonamido)ethylaniline sulfate hydrate, 4-amino-3-methyl-N-ethyl-N-$\beta$-hydroxyethylaniline sulfate, 4-amino-3-$\beta$-(methanesulfonamido)ethyl-N,N-diethylaniline hydrochloride and 4-amino-3-methyl-N-ethyl-N-(2-methoxyethyl)aniline-di-p-toluenesulfonic acid.

With negative working silver halide, the processing step described above gives a negative image. To obtain a positive (or reversal) image, this step can be preceded by development with a non-chromogenic developing agent to develop exposed silver halide, but not form dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following examples are included for a further understanding of this invention.

EXAMPLE 1

Preparation of Bis(1,1-diethylpropyl) Phthalate (Compound 1)

To a solution of 23.2 g (0.2 mol) 3-ethyl-3-pentanol in 50 mL tetrahydrofuran, stirred at 0° C. under nitrogen, was added dropwise 92 mL of a 2.4M n-butyllithium solution in hexane. Stirring was continued 30 min. as the mixture warmed to room temperature. Then, a solution of 20.3 g (0.1 mol) phthaloyl chloride in 10 mL tetrahydrofuran was added to form lithium chloride as a white precipitate. After addition of 40 mL water, the product was isolated as a viscous liquid to give 32.3 g (89% yield) of Compound 1, confirmed by an nmr spectrum.

The same procedure, but replacing the 3-ethyl-3-pentanol with 31 g (0.2 mol) α-terpineol, provided 35 g (79.5% yield) of a very viscous light yellow liquid shown by nmr to be Compound 4.

EXAMPLE 2

Preparation of Bis(2-n-butylfenchyl) Phthalate (Compound 7)

To a solution of 30.5 g (0.2 mol) 1-fenchone in 50 mL tetrahydrofuran, stirred at 0° C. under nitrogen, was added dropwise 95 mL of a 2.2M n-butyllithium solution in hexane. Stirring was continued overnight as the mixture warmed to room temperature. Then a solution of 22.3 g (0.11 mol) phthaloyl chloride in 15 mL tetrahydrofuran was slowly added to form lithium chloride as a white precipitate. Addition of 20 mL water, isolation of product and purification by silica gel chromatography gave, as a first fraction, 2.3 g crystalline Compound 7, m.p. 153°-6° C., confirmed by an nmr spectrum.

EXAMPLE 3

Preparation of Bis(1-ethyl-1,5-dimethylhexyl) Phthalate (Compound 6) by Hydrogenation of Dilinalyl Phthalate A solution of 10 g (22.8 mmol) dilinalyl phthalate (prepared by the procedure of Example 1) in 100 mL tetrahydrofuran was treated with 2 g palladium on charcoal catalyst and hydrogenated quickly at 40 psi. A small amount of cleavage gave some phthalic acid by-product, so the mixture was chromatographed on silica gel to give 7.1 g (70% yield) of pure viscous liquid Compound 6, confirmed by its nmr spectrum.

EXAMPLE 4

Ferrous Ion Stability Tests

Photographic elements were prepared by coating a gel-subbed, polyethylene-coated paper support with a photosensitive layer containing a silver bromoiodide emulsion at 0.28 g Ag/$m^2$, gelatin at 1.62 g/$m^2$, and dispersions containing each of the coupler/solvent combinations described in Table 1. Coupler solvents of the invention were employed along with various comparison solvents (CS) as controls.

The cyan coupler coverage was 1.26 millimoles/$m^2$ and the weight of coupler solvent was half that of the coupler.

The photosensitive layer was overcoated with a layer containing gelatin at 1.08 g/$m^2$ and bisvinylsulfonylmethyl ether hardener at 2 weight percent based on total gelatin.

Cyan Couplers Employed

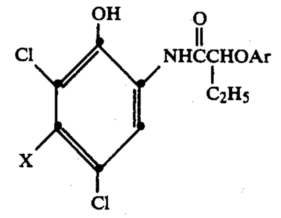

| Coupler | X | Ar |
|---|---|---|
| A | $-CH_3$ | 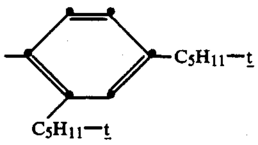 |
| B | $-C_2H_5$ | 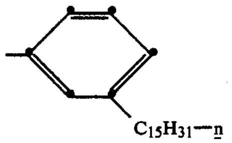 |
| C | $-CH_3$ | 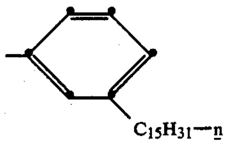 |

Comparison Coupler Solvents

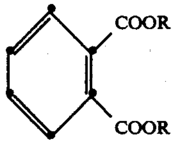

| Comparison Coupler Solvent | R |
|---|---|
| CS-1 | $-CH_3$ |
| CS-2 | $-C_3H_7-\underline{n}$ |
| CS-3 | $-C_4H_9-\underline{n}$ (U.S. Pat. No. 2,322,027) |
| CS-4 | $CH_3CHCH_2CH_3$ |
| CS-5 | $-C(CH_3)_3$ (Research Disclosure 16744, March 1978) |
| CS-6 | $-CH_2CH(CH_3)_2$ |
| CS-7 | $-CH_2C(CH_3)_3$ |
| CS-8 | $CH_3CH(CH_2)_3CH_3$ |
| CS-9 | $-C_8H_{17}-\underline{n}$ |

-continued

Comparison Coupler Solvents

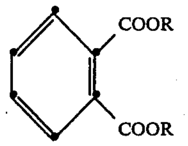

| Comparison Coupler Solvent | R |
|---|---|
| CS-10 | $CH_3CH(CH_2)_5CH_3$ |
| CS-11 | $-CH_2CHC_4H_9$ / $C_2H_5$ |
| | (British Patent 1,274,523) |
| CS-12 | $-C_{12}H_{25}-\underline{n}$ |
| CS-13 | 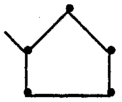 |
| | (U.S. Pat. Nos. 4,193,802 and 4,327,175) |
| CS-14 | 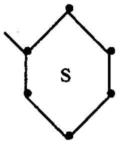 |
| | (U.S. Pat. Nos. 4,193,802 and 4,327,175) |
| CS-15 | 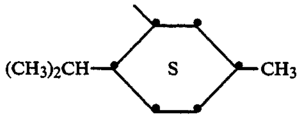 |
| | (U.S. Pat. Nos. 4,193,802 and 4,327,175) |
| CS-16 | $CH_2=CHCCH_2CH_2CH=CCH_3$ (with $CH_3$ on each of the two C) |

Samples of each element were imagewise exposed through a graduated-density test object, processed at 33° C. employing the color developer identified below, then 1.5 minutes in the bleach-fix bath, washed and dried.

| Color Developer (pH 10.08) | |
|---|---|
| Triethanolamine | 11 mL |
| Benzyl alcohol | 14.2 mL |
| Lithium chloride | 2.1 g |
| Potassium bromide | 0.6 g |
| Hydroxylamine sulfate | 3.2 g |
| Potassium sulfite (45% solution) | 2.8 mL |
| 1-Hydroxyethylene-1,1-di-phosphoric acid (60%) | 0.8 mL |
| 4-Amino-3-methyl-N—ethyl-N—β-methanesulfonamido)ethyl-aniline sulfate hydrate | 4.35 g |
| Potassium carbonate (anhydrous) | 28 g |
| Stilbene whitening agent | 0.6 g |
| Surfactant | 1 mL |
| Water to make | 1.0 liter |
| Bleach-Fix Bath (pH 6.8) | |
| Ammonium thiosulfate | 104 g |
| Sodium hydrogen sulfite | 13 g |
| Ferric ammonium ethylenediamine tetraacetic acid (EDTA) | 65.6 g |
| EDTA | 6.56 g |
| Ammonium hydroxide (28%) | 27.9 mL |
| Water to make | 1 liter |

Density measurements were then made on a densitometer.

Processed strips of each element containing a dye image were then subjected to a 5 minute immersion in the following:

| 0.1 M Ferrous Ion Solution (made under nitrogen purging) | |
|---|---|
| Degassed distilled water | 750 mL |
| EDTA | 32.12 g |
| Ammonium hydroxide conc. solution) | 15 mL |
| Ferrous sulfate.7 $H_2O$ | 27.8 g |
| Ammonium hydroxide and water to: | 1.0 L |
| (Nitric acid to adjust pH downward) | pH 5.0 |

Density measurements on a densitometer were again made and a density loss was observed for each of the elements as follows:

TABLE 1

| Cyan Coupler | Coupler Solvent | Density Loss (%) |
|---|---|---|
| C | CS-3 | 55 |
| | Compound 2 | 32 |
| B | CS-3 | 67 |
| | CS-8 | 49 |
| | CS-13 | 36 |
| | Compound 8 | 23 |
| B | CS-3 | 57 |
| | CS-6 | 40 |
| | CS-9 | 39 |
| | CS-2 | 35 |
| | CS-1 | 31 |
| | CS-14 | 18 |
| | Compound 7 | 11 |
| B | CS-3 | 53 |
| | CS-5 | 14 |
| | CS-16 | 11 |
| | Compound 24 | 10 |
| | Compound 6 | 9 |
| | Compound 1 | 7 |
| | Compound 4 | 6 |
| | Compound 5 | 6 |
| | Compound 10 | 3 |
| B | CS-3 | 52 |
| | CS-7 | 18 |
| | Compound 9 | 12 |
| B | CS-3 | 50 |
| | CS-11 | 30 |
| | Compound 2 | 20 |
| B | CS-3 | 39 |
| | Compound 3 | 14 |
| A | CS-3 | 13 |
| | CS-12 | 12 |
| | Compound 2 | 11 |

In every case, the coupler solvents of the invention were much more effective in preventing ferrous ion reduction of cyan dye than closely-related comparison coupler solvents.

EXAMPLE 5

Yellow Dye Light Stability Improvement

Photographic elements were prepared and processed as in Example 4 except that the coatings contained 0.40 g $Ag/m^2$, 1.09 millimole/$m^2$ of a yellow dye-forming coupler, and one-fourth the coupler weight of the coupler solvents listed in Table 2.

yellow dye-forming coupler

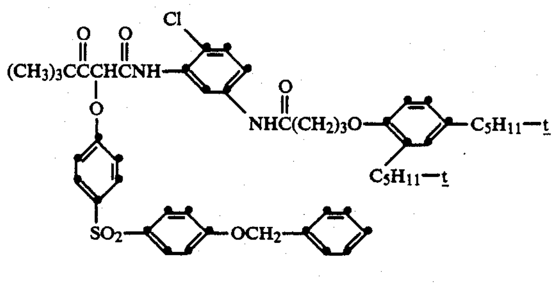

Densitometric curves were obtained before and after fading for step-wedge exposed strips and density losses were measured. Both shoulder (step 7) and Dmax (step 2) densities of each curve were compared. Fading was accomplished using either a 50 Klux or 5.4 Klux xenon source, the ultraviolet component of which was removed using a Wratten 2B filter. The following results were obtained:

TABLE 2

| | Density Loss 2 wk. 50 Klux | | Density Loss 24 wk. 5.4 Klux | |
|---|---|---|---|---|
| Coupler Solvent | shoulder (%) | Dmax (%) | shoulder (%) | Dmax (%) |
| CS-3 | 22.3 | 39.8 | 22.1 | 35.6 |
| CS-11 | 12.8 | 22.8 | 12.0 | 18.1 |
| Compound 2 | 9.5 | 16.3 | 8.9 | 12.6 |
| CS-3 | 18.8 | 24.9 | 16.2 | 15.5 |
| CS-16 | 18.2 | 17.8 | 11.4 | 10.6 |
| CS-5 | 11.2 | 13.3 | 8.6 | 7.7 |
| Compound 24 | 10.9 | 10.3 | 6.4 | 3.8 |
| Compound 1 | 9.8 | 9.4 | 6.6 | 4.7 |
| Compound 4 | 8.8 | 10.3 | 6.0 | 4.1 |
| Compound 5 | 7.9 | 5.2 | 6.0 | 7.6 |
| Compound 6 | 8.9 | 8.0 | 6.3 | 6.2 |
| Compound 10 | 9.3 | 8.6 | 6.8 | 5.7 |
| Compound 7 | 9.3 | 7.6 | 6.5 | 5.1 |

The data show that a yellow dye formed from an incorporated coupled dispersed in the coupler solvents of the invention had markedly improved light stability over the same dye formed in the presence of the comparison coupler solvents.

EXAMPLE 6

Cyan Dye Dark Stability Improvement

Photographic elements were prepared and processed as in Example 4. Then, strips containing step images of cyan dyes formed from dispersions of coupler/solvent combinations as indicated in Table 3 were subjected to accelerated tests conducted for the indicated times in dark ovens at either 60° C./70% R.H. or 77° C./5% R.H. Density losses were measured after the keeping tests. The following results were obtained:

TABLE 3

| | Density Loss from D = 1.7 | | | |
|---|---|---|---|---|
| | 6 weeks @ | 3 weeks @ 77° C./5% R.H. | | |
| Coupler Solvent | 60° C./70% R.H. Compound A | Coupler A | Coupler B | Coupler C |
| CS-3 | −.26 | −.48 | −.22 | −.20 |
| CS-4 | — | — | −.24 | — |
| CS-8 | −.23 | −.39 | — | — |
| CS-11 | −.23 | −.39 | −.21 | −.15 |
| Compound 2 | −.17 | −.35 | −.20 | −.16 |

The data show that a coupler solvent of the invention provided improved cyan dye dark stability in color photographic coatings.

EXAMPLE 7

Magenta Dye Stability Improvement

Photographic elements were prepared and processed as in Example 4, except that the silver bromoiodide emulsion was coated at 0.51 g $Ag/m^2$ with 0.66 millimoles/$m^2$ of a magenta coupler dispersed in half its weight of coupler solvent as indicated in Table 4 plus 0.39 g/$m^2$ chromanol stabilizer (Compound 7 of U.S. Pat. No. 3,432,300).

magenta coupler

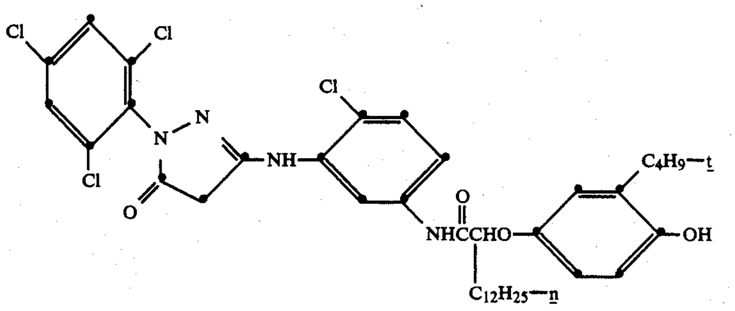

Density changes were measured after light and dark fading tests similar to those described in Examples 5 and 6. The following results were obtained:

TABLE 4

| | Density Change from D = 1.7 | | | |
|---|---|---|---|---|
| Coupler Solvent | 2 wk.* 50 Klux | 24 wk.* 5.4 Klux | 6 wk. 60° C./ 70% R.H. | 2 wk. 77° C./ 5% R.H. |
| TCP** | −.39 | −.57 | +.02 | −.16 |
| CS-4 | −.41 | −.51 | +.09 | −.17 |
| CS-15 | −.35 | −.44 | +.02 | −.11 |

TABLE 4-continued

| Coupler Solvent | Density Change from D = 1.7 | | | |
|---|---|---|---|---|
| | 2 wk.* 50 Klux | 24 wk.* 5.4 Klux | 6 wk. 60° C./ 70% R.H. | 2 wk. 77° C./ 5% R.H. |
| Compound 2 | −.33 | −.40 | −.02 | −.18 |

*A Wratten 2B filter removed UV light in these fade tests.
**TCP = tricresyl phosphate The data show that a coupler solvent of the invention gave improvements over comparison coupler solvents for magenta dye stability to heat and light while maintaining at least comparable stability to humidity.

The invention has been described in detail with particular reference to preferred embodiments thereof, but it will be understood that variations and modifications can be effected within the spirit and scope of the invention.

What is claimed is:

1. A compound which has the formula:

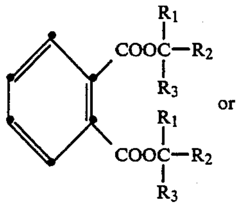

or

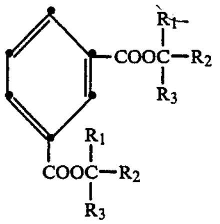

wherein $R_1$, $R_2$, and $R_3$ each independently represents a substituted or unsubstituted alkyl group having from 1 to about 10 carbon atoms; a substituted or unsubstituted alicyclic group, saturated or partially saturated, having from 3 to about 12 carbon atoms; a substituted or unsubstituted aralkyl group having from about 7 to about 20 carbon atoms; a substituted or unsubstituted aryl group having from about 6 to about 20 carbon atoms; a substituted or unsubstituted heterocyclyl group having from 3 to about 10 carbon atoms; or may be combined together to form one or more rings;

with the proviso that the alpha hydrogens of $R_1$, $R_2$, and $R_3$ total no more than seven; and with the further proviso that $R_1$ can additionally be hydrogen when (a) $R_2$ and $R_3$ join together to form a ring substituted by no more than one alpha hydrogen or (b) $R_2$ and $R_3$ do not join to form a ring and if at least one of $R_2$ or $R_3$ contains an alpha carbon having two different non-hydrogen substituents.

2. The compound of claim 1 wherein $R_1$ is hydrogen or an alkyl group of from 1 to about 10 carbon atoms, $R_2$ is an alkyl group of from 1 to about 10 carbon atoms, $R_3$ is an alkyl or substituted alkyl group of from 2 to about 12 carbon atoms or an aryl or substituted aryl group of 6 to about 20 carbon atoms, or $R_2$ and $R_3$ are combined together to form a ring of about 4 to about 10 atoms.

3. The compound of claim 1 wherein $R_1$ and $R_2$ are the same or different alkyl or substituted alkyl groups containing from 1 to about 10 carbon atoms and $R_3$ is an alkyl group containing from 2 to about 12 carbon atoms.

4. The compound of claim 1 wherein $R_1$ is an alkyl group of from 1 to about 10 carbon atoms and $R_2$ and $R_3$ are combined together to form a ring of 6 carbon atoms.

5. The compound of claim 1 wherein $R_1$, $R_2$ and $R_3$ are each ethyl.

6. The compound of claim 1 wherein $R_1$ is hydrogen or methyl, $R_2$ is methyl, and $R_3$ is

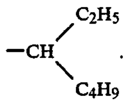

7. The compound of claim 1 wherein $R_1$ and $R_2$ are each methyl and $R_3$ is

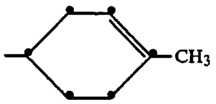

or

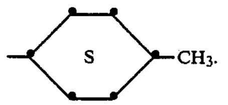

8. The compound of claim 1 wherein $R_1$ is ethyl, $R_2$ is methyl and $R_3$ is $—CH_2CH_2CH_2CH—CH_3$.

9. The compound of claim 1 wherein $R_1$ is hydrogen or butyl and $R_2—C—R_3$ forms the fenchyl group

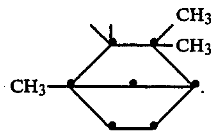

10. The compound of claim 1 wherein $R_1$ is methyl and $R_2$ and $R_3$ form a cyclohexyl ring.

11. The compound of claim 1 wherein $R_1$ is methyl and $R_2—C—R_3$ forms the menthyl group

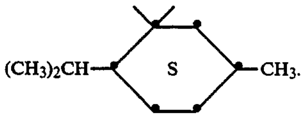

12. The compound of claim 1 wherein $R_1$ is hydrogen, $R_2$ is methyl and $R_3$ is phenyl.

* * * * *